United States Patent [19]

Tanaka et al.

[11] 4,309,611
[45] Jan. 5, 1982

[54] SCANNER FOR POSITRON EMISSION COMPUTED TOMOGRAPHY

[75] Inventors: Eiichi Tanaka, Mitaka; Norimasa Nohara; Takehiro Tomitani, both of Chiba; Kenji Ishimatsu, Abiko; Katsumi Takami, Tokyo, all of Japan

[73] Assignees: National Institute of Radiological Sciences, Chiba; Hitachi Medical Corporation, Tokyo, both of Japan

[21] Appl. No.: 109,252

[22] Filed: Jan. 3, 1980

[30] Foreign Application Priority Data

Jan. 12, 1979 [JP] Japan .................................. 54-1228

[51] Int. Cl.³ .............................................. G01T 1/20
[52] U.S. Cl. ................................. 250/363 S; 250/366
[58] Field of Search .................... 250/360, 363 S, 366, 250/369, 445 T

[56] References Cited

U.S. PATENT DOCUMENTS

| | | | |
|---|---|---|---|
| 3,594,577 | 7/1971 | Loveday | 250/363 S |
| 3,970,853 | 7/1976 | Kuhl et al. | 250/363 S |
| 4,213,054 | 7/1980 | Doherty | 250/363 S |

*Primary Examiner*—Alfred E. Smith
*Assistant Examiner*—Janice A. Howell
*Attorney, Agent, or Firm*—Gerald J. Ferguson, Jr.; Joseph J. Baker

[57] ABSTRACT

A scanner for positron emission computed tomography comprising a rotary member rotatable within the plane of a slice about an axis lying perpendicular to this plane and having means for accommodating a subject for examination, a drive means for rotating this rotary member within the plane of slice, and a plurality of radiation detectors provided on the rotary member so as to substantially face each other relative to the subject to be examined, in which the radiation detectors are disposed so that at least some of them are either positioned with irregular spacing relative to each other, or positioned at irregular distances from the axis of rotation.

24 Claims, 31 Drawing Figures

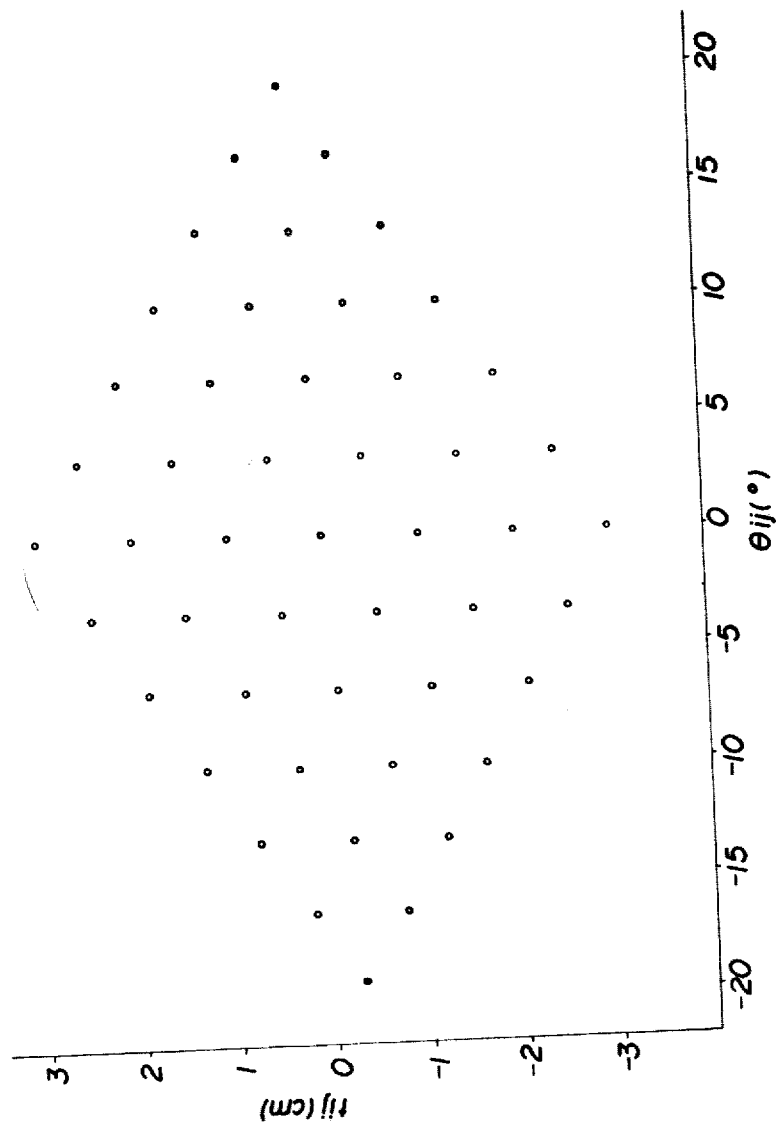

SCANNER FOR POSITRON EMISSION COMPUTED TOMOGRAPHY

BACKGROUND OF THE INVENTION (a) Field of the Invention:

The present invention concerns a scanner for positron emission computed tomography, and more particularly it pertains to an improvement of the arrangement of the detectors employed in this scanner.

(b) Description of the Prior Art:

There have been proposed apparatuses for measuring, externally of the subject to be examined, of intra-body distribution of positron-emitting radioisotopes which are administered into the body of the subject, and those apparatuses designed for displaying images of a slice on a cathode ray tube.

FIG. 1 schematically shows such known apparatus. In FIG. 1, reference numeral 1 represents a subject for examination. 2 represents respective gamma ($\gamma$) ray detectors (hereinafter to be referred to briefly as detectors). 3 represents an array of detectors which is constructed by a row of a plurality of detectors. 4 represents a coincidence counting circuit. 5 represents a data collecting and recording means. 6 represents a data processing means. 7 represents an image display means. The detectors included in the array 3 of detectors are disposed on a plane containing a slice of the subject 1 for examinatior, and they are assigned to detect gamma rays due to the isotopes contained in the body of the subject 1.

The isotope which is administered into the body of subject 1 is selected from those substances, such as carbon 11 ($^{11}C$), nitrogen 13 ($^{13}N$) and fluorine 18 ($^{18}F$) which emit positrons. Positrons which are emitted from atomic nuclei of the isotopes cause annihilation reaction with the electrons which are present at sites very close to those positrons emitted. As a result, there are generated two annihilation gamma photons which are emitted in opposite directions at the same time. Let us now suppose that two of the detectors 2, each representing one in the respective arrays 3 of detectors which are provided on both sides of the subject 1 in FIG. 1 have detected annihilation gamma photons at the same time. Then, the positions at which these annihilation gamma ray photons are generated, i.e. approximately the positions of the isotope atoms which have emitted positrons, are considered to be on the straight line connecting these two detectors. It should be understood that each of those solid lines connecting two detectors which are contained in the respective arrays 3 of detectors represents an imaginary straight line passing through the position of the isotope atom which is found by detecting the coincidence count performed by the two detectors connected by that straight line. The position of the isotope atom which is found out can be designated by the positional coordinate of the opposing two detectors which participate in the coincidence counting. It should be understood, however, that such position of the isotope atom which is found out may be designated also by the two factors, i.e. the distance t from the origin of an appropriate coordinate system which is fixed in the subject 1 and which lies in a plane containing the arrays 3 of detectors to the aforesaid imaginary rectilinear line and which has the coordinate origin at the center of rotation, and the angle $\theta$ defined by this imaginary rectilinear line relative to an axis of coordinate. In this specification, the position of the isotope atom which is detected is represented by a rectilinear line connecting two detectors, and it is expressed by the distance t and the angle $\theta$, and such position is called a sample position or sampling position, and the aforesaid two detectors which are electrically connected by a coincidence counting circuit for detecting a coincidence count are called a detector pair. The emission of positron which is thus detected by an appropriate detector pair connected together by a coincidence counting circuit is recorded of its number of count and sampling position (t, $\theta$), by a data-collecting-and-recording means 5. Those data which thus have been recorded within a certain period of time and then subjected to rearrangement and reconstruction of the data at a data processing means 6, whereby an image of distribution of isotopes in that portion of the body of subject which is sliced at said plane, i.e. a cross-sectional image, is synthesized, and it is displayed by an image indicating means 7.

FIG. 2 shows an arrangement of detectors in a known scanner for positron emission computed tomography which is based on the foregoing principle. In FIG. 2, there are depicted thirty six (36) detectors to facilitate understanding. It should be noted, however, that in practice there are arranged 60~200 detectors. In this known apparatus, detectors 2 are arranged with equal spacing on a circular circumference surrounding the subject 1, and these detectors are connected to coincidence counting circuits for detecting coincidence counts between them and those detectors which are located on the other side relative to the center C of the circular circumference. It should be understood that a certain detector located on this side is not coupled to only one detector located on the other side to make a pair, but to a plurality of detectors via a coincidence counting circuit. All of those detectors which are located on the other side relative to a certain designated detector located on this side, and which are located within the range of coverage by this certain detector are coupled to this certain detector by coincidence counting circuits, respectively. For example, the certain designated detector is coupled, by coincidence counting circuits, to all of those detectors which lie within an angle $+30°$ as viewed from this certain detector relative to the rectilinear line connecting this certain detector and the center C of the aforesaid circular circumference.

A scanner having such arrangement of detectors as stated above is capable of making detection as well as coincidence counting of those gamma ray pairs which are emitted at arbitrary positions lying within a circle of a radius which is about ½ of the radius of the circular circumference on which the detectors are arranged, without requiring mechanical movement such as rotation of the arrays of detectors, and thus the scanner is able to determine their sampling positions (t, $\theta$).

In such known scanner, the values of t which are obtained represent discontinuous descrete values having distance intervals substantially equal to the spacing of the detectors. On the other hand, the values of $\theta$ obtained are only discontinuous discrete values with intervals representing an angle defined by a detector and adjacent two detectors which are located on the other side relative to the center C. Apart from the above, the smaller the respective intervals of the values t and of the values $\theta$ are, the higher can be improved the quality of the image which is reconstructed. Thus, with such known apparatus, it is not possible to obtain intervals of t or θ which are sufficient for obtaining a quality image. Also, if a large number of detectors are arranged to make the intervals of θ or of t sufficiently small, it will be obvious that the cost of manufacture will be increased markedly.

On the other hand, there has been proposed to improve the quality of image, in this known apparatus, by first taking a measurement once at a stationary state of the apparatus, and thereafter repeating the measurement after revolving the arrays of detectors through an angle which is $\frac{1}{2}$ of the angle defined by the center C and adjacent two detectors located on one side relative to this center C, thereby making the respective intervals of t and of $\theta\frac{1}{2}$ relative to the intervals obtained at the time of measurement at stationary state of the arrays of detectors. It should be understood, however, that even from further continuation of such revolution, it is not possible to reduce the intervals of t and of θ any further. Furthermore, even when a measurement is taken by making the angle of one revolution sufficiently small, there will arise no change in the intervals of t which control the resolution of image, though the intervals of θ will become reduced accordingly.

SUMMARY OF THE INVENTION

It is the object of the present invention to seek a scanner for positron emission computed tomography, which is such that the distance t of a sampling position (t, θ) can have a number of different values.

It is another object of the present invention to provide a scanner for positron emission computed tomography comprising: a rotary member rotatable about an axis lying and perpendicular to this slice plane having means for accomodating a subject for examination, a drive means for rotating this rotary member within the plane of slice, and a plurality of radiation detectors provided on the rotary member with the intervention by the center of rotation of this rotary member, said radiation detectors being disposed so that at least some of them are positioned with irregular spacing relative to each other, or at uneven distances from the axis of rotation.

BRIEF DESCRIPTION OF THE DRAWINGS

FIGS. 3 and 4 show an example of the positron emission computed tomographic apparatus according to the present invention, in which:

FIG. 3 is a vertical sectional view of the scanning device, and

FIG. 4 is an enlarged front view of the gamma ray detector unit taken along the line V—V in FIG. 3.

FIGS. 7 and 8 are graphs showing the distribution of sampling positions obtained, in which:

FIG. 7 is a graph showing the distribution of sampling positions obtained from a known detector arrangement and FIG. 8 is a graph showing the distribution of sampling positions obtained from the detector arrangement according to the present invention.

FIG. 31 is a graph showing the distribution of the sampling positions obtained from the detector arrangement shown in FIG. 30.

DETAILED DESCRIPTION OF THE PREFERRED EMBODIMENTS

Figure 3:
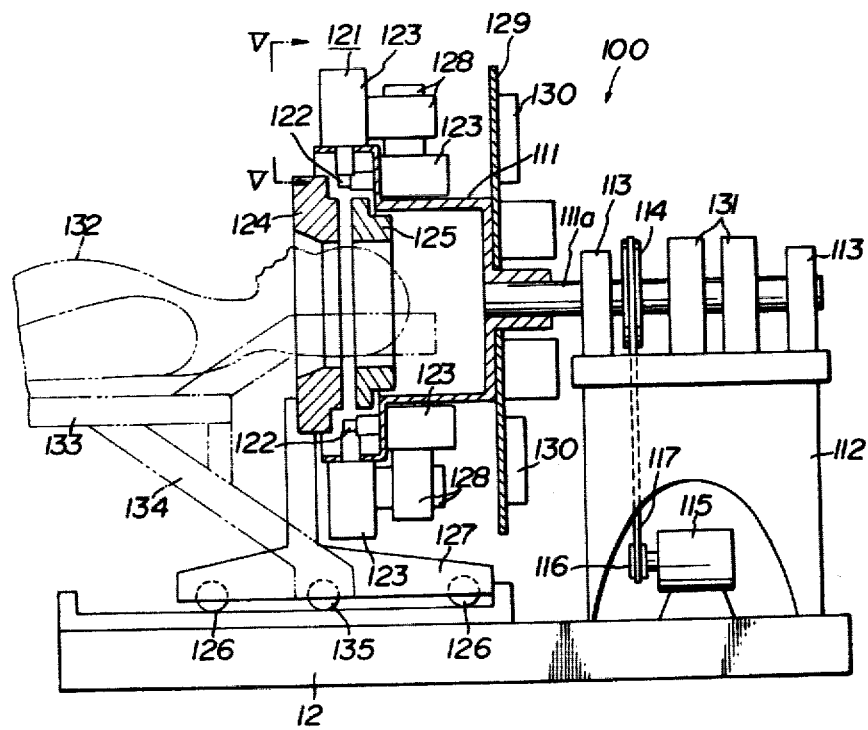
Figure 4:
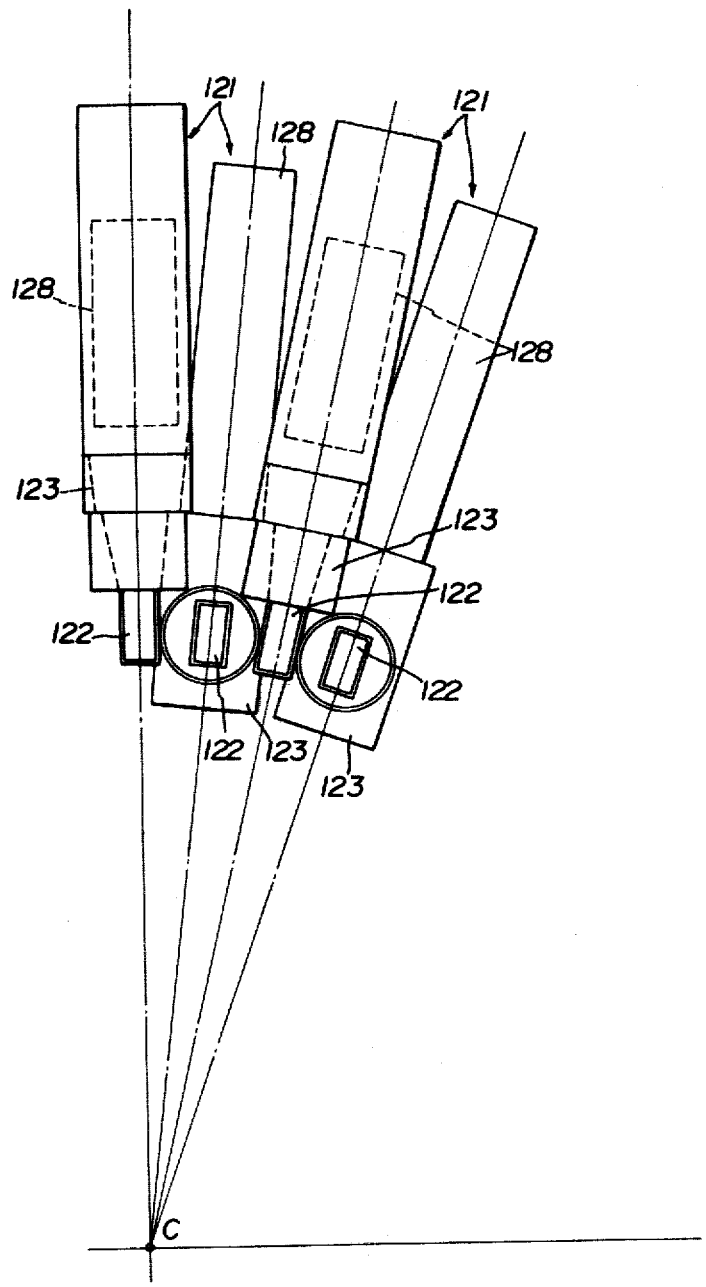

FIGS. 3 and 4 show an example of concrete structure of the scanner according to the present invention. The scanner has a rotary frame 111. This rotary frame has a body which is substantially hollow cylindrical configuration. A side plate is fixed to one of the open ends of this body. A shaft 111a is received in and fixed to, at its one end, this side plate. The opposite end portion of this shaft is supported on a bearing 113 which is provided on a pedestal 112. A belt-pulley 114 is mounted on the shaft 111a. This belt-pulley 114 is coupled, by a belt 117 such as a synchronous drive belt, to a belt-pulley 116 which is mounted on a rotary shaft of an electric motor 115 provided on the pedestal, so that the rotary frame is adapted to be rotated by the electric motor.

A gamma ray detecting unit 121 is arranged along the circumference of the rotary frame 111. The respective gamma ray detectors of the unit are each comprised of a scintillator 112 and a photomultiplier tube 123, so that the scintillator is adapted to emit fluorescent light by the irradiation of gamma rays thereto, and that the photomultiplier tube is adapted to output a pulse which is proportional to the intensity of the fluorescent light. The respective scintillators are arranged so that they are located in an imaginary plane or slice plane which intersects, at right angle, the central axis C of rotation of the rotary frame 111. In this scanning device, the photomultiplier tubes of any adjacently located detectors are arranged to cross each other at right angle, so that gamma ray detectors can be disposed close to each other, that the gamma ray detection sensitivity is enhanced, and that the device as a whole is constructed compact. A collimator is comprised of two ring-shaped members 124 and 125. These two ring-shaped members are disposed to oppose each other to form a gamma ray passageway, and are supported on a stand 127 having wheels 126. The respective gamma ray detectors are electrically connected to pre-amplifiers 128 which, together with these gamma ray detectors, are provided on the rotary frame 111. The respective pre-amplifiers are connected to coincidence counting circuits 130 which are provided on a supporting plate 129 which, in turn, is fixed to the rotary frame, in such way that each detector will perform coincidence counting with all those detectors which are covered within its view angle, i.e. the angular range which this detector is able to detect. The coincidence counting circuit is connected, via a pre-processing device not shown and a signal transmission device 131 such as slip ring, to a data processing device which, jointly with the scanner, constitutes positron emission computed tomographic apparatus.

The subject for examination 132 is placed on a bed 133, and is moved so that the required cross-sectional plane or slice plane for examination of this subject will be brought into agreement with the aforesaid plane in which the gamma ray detectors are arrayed. The bed-supporting base 134 is provided with wheels 135 for effecting such movement. Upon starting the electric motor 115, the rotation of this motor rotates the rotary frame 111 via the pulleys and the belt. Those positrons which are emitted from the isotopes administered into the body of the subject cause annihilation reaction with those electrons which are present nearby. Gamma rays which are generated in this way are irradiated into the gamma ray detectors. These gamma rays are detected by those gamma ray detectors which are coupled by the coincidence counting circuits to form a pair, and they are amplified by the pre-amplifiers. Whereupon, the coincidence counts are discriminated and the coincidence counting circuits deliver an output. These outputs are processed by the pre-processing device about such informations as those related to their sampling positions, and then they are inputted, via a signal transmission device, to a data processing device which, jointly with the scanner and other appliances, constitutes a positron emission computed tomographic apparatus.

Figure 5:
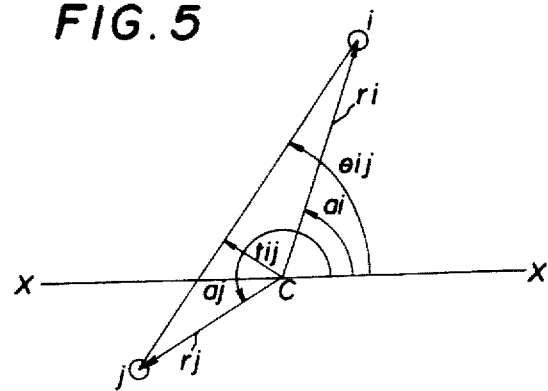
FIG. 5 is an illustration for explaining the arrangement of the detectors in a scanner for positron emission computed tomography according to the present invention.

FIG. 5 is an illustration showing coordinate system for explaining the arrrangement of the detectors in the scanner of the present invention.

Point C and the rectilinear line XX represent the origin and the coordinate axis of the coordinate system which is fixed to the body of the subject for examination. The array of gamma ray detectors is rotated about this point C. Point i and point j represent appropriate gamma ray detectors which make a pair among the array of detectors. $r_i$ and $r_j$ represent the distances from the center C of rotation to the detectors i and j. $a_i$ and $a_j$ represent angles defined by $r_i$ and $r_j$ relative to the axis of coordinate axis XX. $t_{ij}$ and $\theta_{ij}$ represent the distance from point C to the rectilinear line connecting the detectors i and j, and the angle formed by this rectilinear line relative to the coordinate axis XX, i.e. the sampling position of the information obtained by the coincidence counting by the detector pair i and j, respectively. Let us now assume that, with respect to all angles, those angles going counter-clockwise are designated as positive angles, and that those going clockwise are designated as negative angles. Then, the sampling positions $\theta_{ij}$ and $t_{ij}$ of an arbitrary detector are obtained, based on FIG. 5, by the below mentioned formulas:

$$\theta_{ij} = \tan^{-1} \frac{r_i \sin a_i - r_j \sin a_j}{r_i \cos a_i - r_j \cos a_j} \quad (1)$$

$$t_{ij} = -r_i \sin(\theta_{ij} - a_i) \quad (2)$$

The present invention provides that, by taking measurements while rotating the array of detectors relative to the body of subject, i.e. by performing rotary scanning, t is permitted to take a number of values. To this end, the present invention is designed so that, within the possible combination of i and j, that $t_{ij}$ of Formula (2) is able to take as many different values as possible. For this purpose, in Formula (2), $\theta_{ij}-a_i$ are adapted to take different values for the different values of $a_i$, respectively. More particularly, the arrangement of detectors is made so that the detectors are disposed with irregular spacing between detectors, or that they are disposed at different distances from the center of rotation at least locally of the array, to thereby reduce as much as possible the number of those sets of i and j having specific values of angle which is defined by the rectilinear line connecting the detector pair i and j relative to the rectilinear line connecting the detector i and the center C, i.e. $\theta_{ij}-a_i$.

Figure 6:
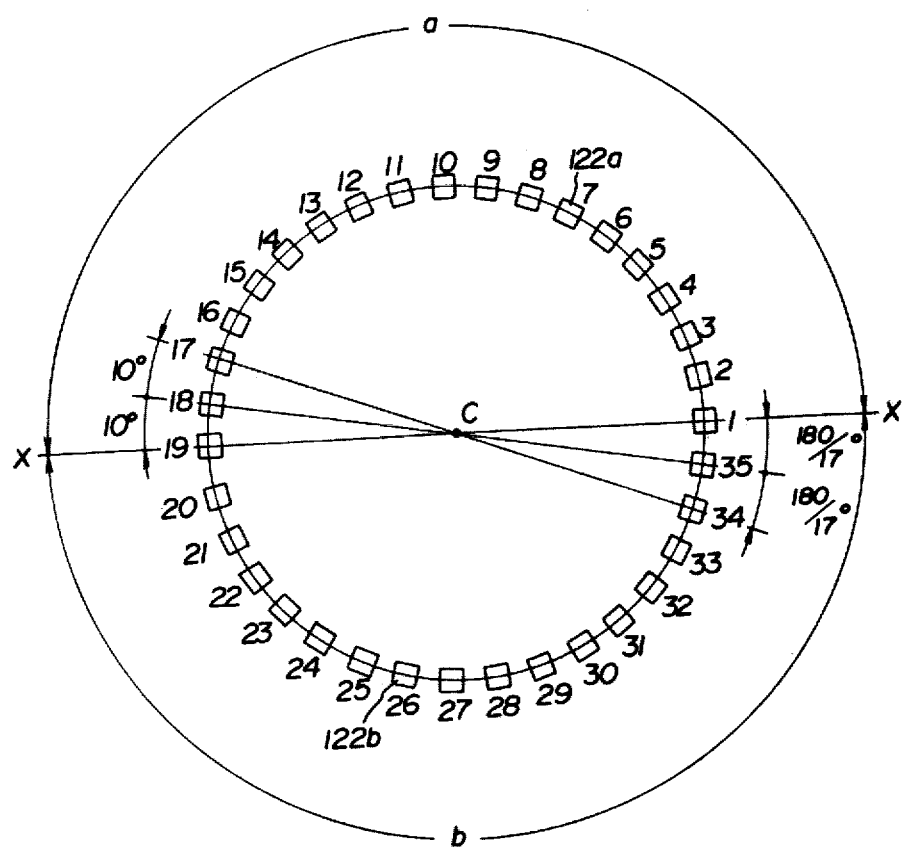
FIG. 6 is an explanatory illustration showing an example of the state in which detectors are arranged.

FIG. 6 shows an example of arrangement of gamma ray detectors. In FIG. 6, only their scintillators are shown. Each gamma ray detector or scintillator 122 is disposed on a single circular circumference lying on a slice plane which crosses, at right angle, the central axis C of rotation of the rotary frame. And, the respective scintillators are distributed in such fashion that eighteen (18) of them are disposed in one a of the two sections divided by an imaginary rectilinear line XX passing through the center C of rotation, i.e. divided by a diametric line, of the aforesaid circle, and seventeen (17) of scintillators are disposed in the other half section b, and that in each of these two sections, the scintillators are disposed with equal spacing. In FIG. 6, those scintillators which are provided in the section a are indicated by a reference numeral 122a, and those in the other section b are indicated by a reference numeral 122b. Also, the respective numbers of the detectors are mentioned by the side of the respective scintillators. Accordingly, those scintillators belonging to section a, i.e. the scintillators 122a from the first to the 18th scintillators, are disposed on one half of circular circumference at respective angle of 10°, whereas those scintillators 122b from the 19th to the 35th which are included in section b are disposed on the other half of the circular circumference at a respective angle of 180/17° (about 10.6°). And, the respective detectors are connected to the coincidence counting circuits in such way that each of them makes detection of coincidence count with respect to those opposing detectors which are located within the angle range of about ±30° relative to the rectilinear line connecting each detector to the center C of rotation.

In an apparatus having such disposition of gamma ray detectors, the distance t and the angle $\theta$ of sampling positions (t, $\theta$) are both able to take a number of different values by rotating either the gamma ray detectors or the rotary frame. This will be described in further detail below.

Figure 7:
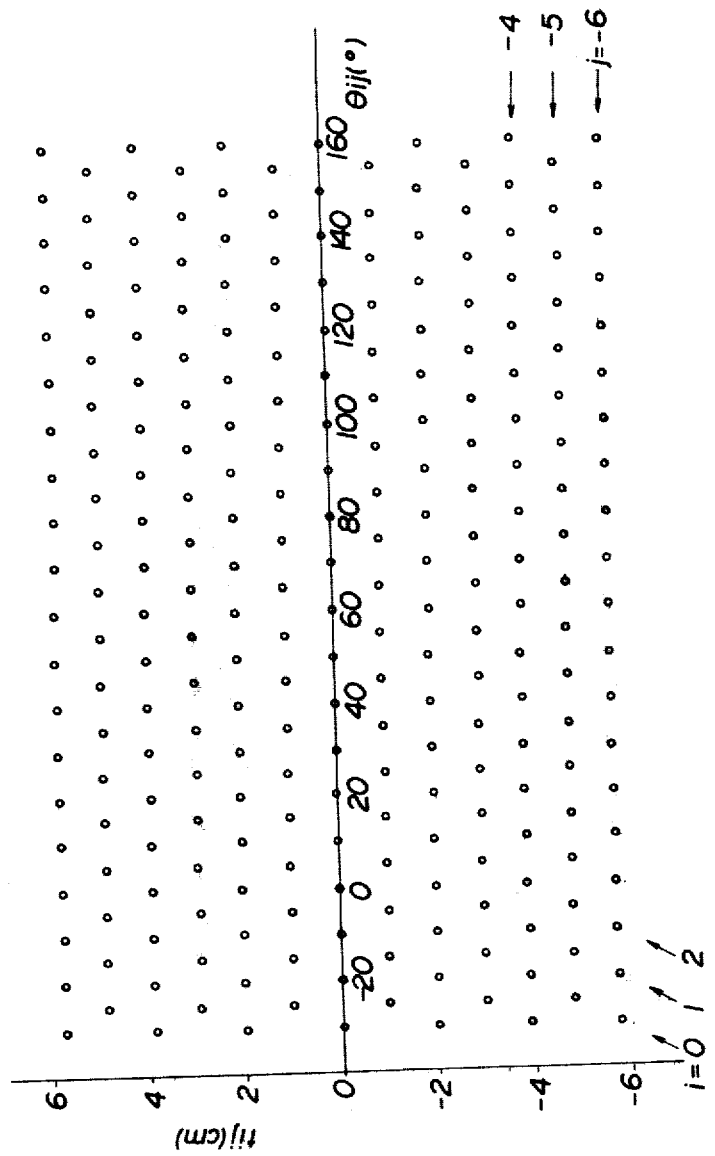
Figure 8:
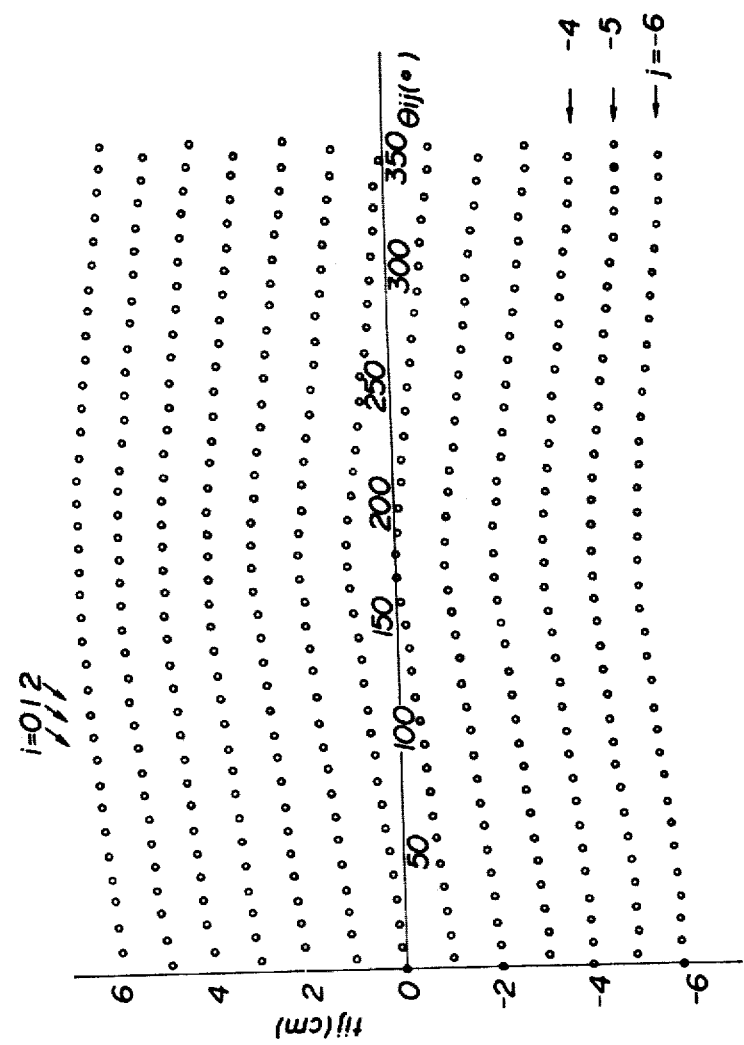

FIGS. 7 and 8 show sampling position distributions of the known apparatus and the apparatus of the present invention, respectively, in case there in no rotation occurring. In these Figures, the vertical axis represents distance t, and the horizontal axis represents angle $\theta$, and the respective sampling positions (t, $\theta$) are shown by small circles. These Figures are provided so that, for the convenience of calculation, the spacing between the detectors is selected at 2 cm and the radium of this aforesaid circle is selected at about 11.5 cm. Also, the visual angle of each detector is set so as to be ±30°. As will be noted from FIG. 7, in the known apparatus, the interval of t at sampling points where $\theta$ is identical, in case the detectors are not rotated, is equal to the spacing of 2 cm between the detectors in the central portion, whereas in the peripheral portion, i.e. in the region where t is large, the interval of t will become slightly smaller than the spacing between the detectors. Also, in case the array of detectors is rotated through an angle of 5° relative to the center C of the circle, i.e. in case the array of detectors is rotated through an angle which is ½ of the spacing between the detectors, and in case data are collected before and after such rotation, the sampling points of the data in this latter case will be exhibited as those obtained by translating or moving the distribution of the former by 5° for the horizontal axis. Accordingly, as will be noted from the Figure, the interval of t when $\theta$ is identical will become ½ of that obtained when the detectors are not rotated. However, even when a further rotation is made, the result is that sampling points are merely superposed, and it is not possible to reduce the interval of t. In the above-stated embodiment, as will be noted from FIG. 8 also, there hardly occurs superposition of sampling points within the range of one whole revolution even when data are collected successively while rotating the detectors. In other words, $t_{ij}$ takes values which are almost different from each other for a given value of position of $a_i$. Therefore, the interval of t is noted to be small as compared with that obtained from the known apparatus. More particularly, in FIG. 7, it will be noted that, even when a measurement is taken after a revolution through 5° by the use of thirty-six (36) detectors, the interval of t remains to be about 1 cm. In contrast thereto, in this embodiment, under the same conditions as those parameters of FIG. 7, excepting the rotation scanning through 360°, and the use of thirty-five (35) detectors, and also the spacing between the detectors in the array, the interval of t is noted to be about 0.05 cm.

The present invention is based on rotation scanning. Therefore, the interval of $\theta$ can be made sufficiently small. If it is assumed that at least one whole revolution is effected, the value of $\theta$ at an arbitrary sampling point in FIG. 8 can have an arbitrary value by rotary scanning, on the one hand, and the value of t can be kept at a certain value which will not vary, since the value of t is not affected by rotation. In such instance, for the purpose of making an evaluation with respect to sampling points, it will be more convenient to project the frequency distribution with respect to all the sampling points t in FIGS. 7 and 8, i.e. to project all this sample points (small circles) in these drawings, onto the vertical axis, and to take a look at the distribution of the number of the projected sampling positions present per unit length of the vertical axis, i.e. the sampling density with respect to t, rather than relying on FIGS. 7 and 8 themselves. By so doing, it becomes possible to evaluate not only the fineness of sampling points, but also the uniformity of sampling density.

Figure 9:
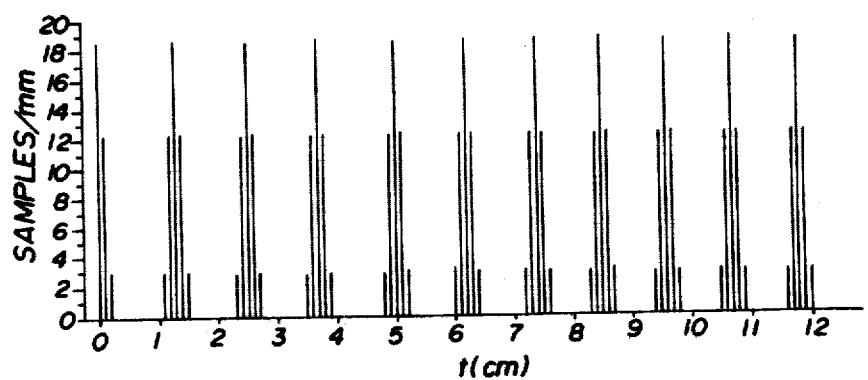
FIG. 9 is a chart showing the frequency distribution of sampling positions t, associated with FIG. 7.
Figure 10:
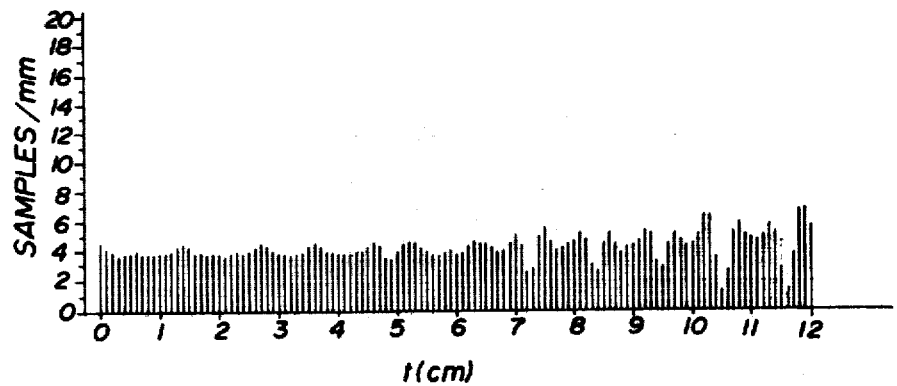
FIG. 10 is a chart showing the frequency distribution of sampling positions t, associated with FIG. 8.

FIGS. 9 and 10 show the distributions of t after some smoothing, i.e. weighted fire-point smoothing. Note that the measured projections are some-times smoothed in order to reduce the noise in the reconstructed image with a slight sacrifice of resolution, and that, in such case, we should consider the distribution of t smoothed in the same manner as above. The horizontal axis represents t, and the vertical axis indicates the number of sampling positions within the range of width of 1 mm of t, i.e. the sampling density with respect to t. The sampling interval with respect to $\theta$ can be reduced by the rotary scanning, as stated previously. On the basis of rotary scanning as in the present invention, it may be said that the largeness of the sampling interval determines the quality of the scanning mechanism. The horizontal axis indicates the distance from the center of rotation of the detector, i.e. from the center of effective filed of view. Therefore, if there is a segment (bar graph) showing the presence of a projection of a number of samples at the position 5 cm on the horizontal axis, this will indicate a sufficient sampling of the informations concerning the radioisotopes which are located on the circular circumference of a radius of 5 cm. If, however, there is no segment at the position 5.5 cm, the data on the circular circumference indicate the absence of at least those samplings which are depicted as rectilinear lines tangential with this circular circumference. In case a distribution of such pattern of presence and absence of segment on the horizontal axis is repeated, this will mean that samplings with respect to t are conducted skipwise and coarsely. On the other hand, in case segments of a same length are arrayed densely on the horizontal axis, this means that the informations concerning all the positions lying within the field of view are collected uniformly with no unevenness, indicating that the scanning mechanism is the most desirable one. FIG. 9 is for the known apparatus having fifty (50) detectors disposed with equal spacing on a circular circumference of a radius of 20 cm.

The distribution of t in this known apparatus is that sampling occurs only at every about 1.2 cm. It should be noted that the sampling positions distributed through a width of 4 mm with spacing of every 1 mm to form one peak pattern is due to the effect of smoothing.

FIG. 10 is for the instance wherein detectors are distributed in such pattern that there are twenty-five (25) detectors disposed in section a and 26 detectors disposed in section b, both with uniform spacing, in order that the result of the present invention shown in FIG. 6 may be compared with that of FIG. 9 which is the result of a conventional apparatus. As will be noted, FIG. 9 shows distribution of intermittent pattern representing the frequency of occurrence at every 1.2 cm. In contrast thereto, FIG. 10 shows a continuous pattern and a considerably uniform distribution. Thus there is an obvious difference between these two.

In the abovementioned embodiment, the number of detectors in sections a and b differ only by one. It is only necessary that the numbers of detectors are different between these two sections. A similar effect can be obtained by the combination of dispositions such as twenty-three (23) detectors and twenty-eight (28) detectors in these two sections, respectively.

Figure 11:
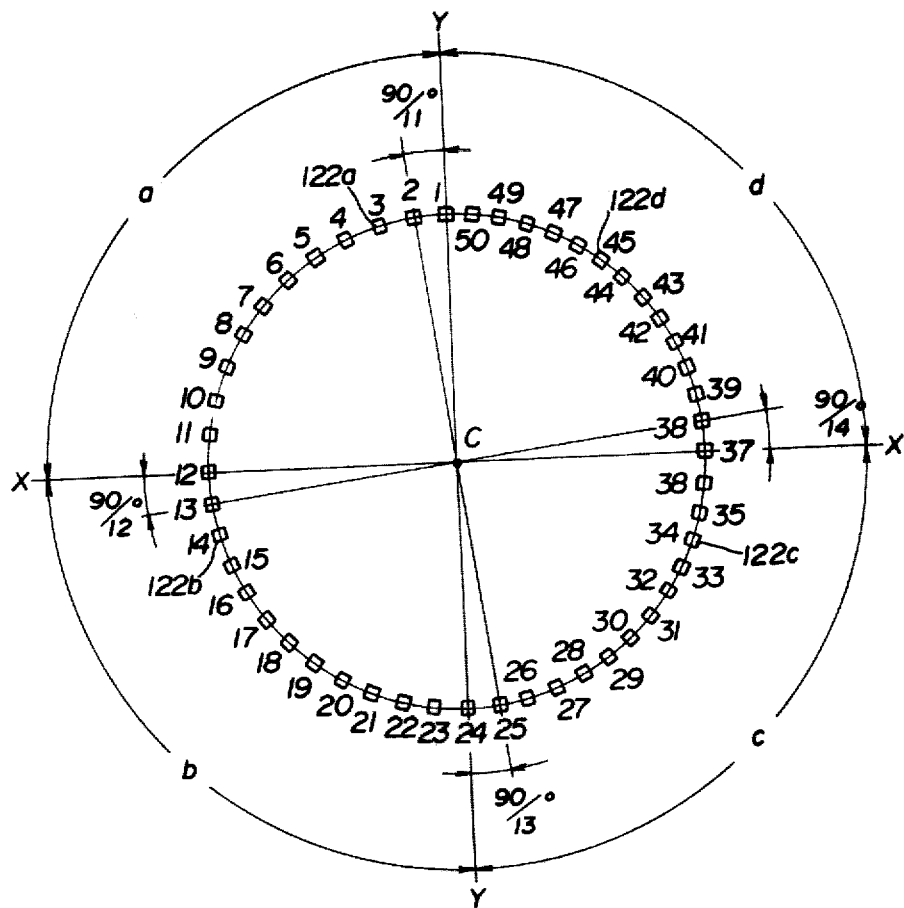
FIG. 11 is an explanatory illustration showing another arrangement of detectors in the scanner of the present invention.
Figure 12:
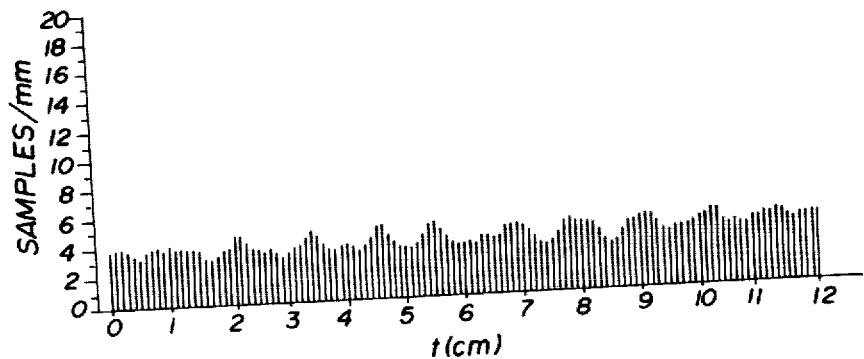
FIG. 12 is an illustration showing the frequency distribution of sampling positions t obtained from the arrangement shown in FIG. 11.

FIG. 11 shows another arrangement of gamma ray detectors of the scanner according to the present invention. In FIG. 11, only scintillators of the detectors are illustrated. In this apparatus, the gamma ray detectors, or more precisely the scintillators 122, are disposed on the plane of slice which intersects at right angle the central axis C of rotation of the rotary frame, and also on a circular circumference co-central with the center C of rotation. However, in this embodiment, the detectors or scintillators are arranged in four sections a, b, c and d which are obtained by dividing by two rectilinear lines XX and YY which pass through the center of rotation and which intersect each other at right angle, and in these four sections a, b, c and d, the detectors are provided in 11, 12, 13 and 14 pieces, respectively, with equal spacing, so that they are rotated about the center C. Because of this arrangement, those respective detectors or scintillators 122a from the first to the 11th in section a each forms an angle of 90/11° relative to the center C. Similarly, those detectors 122b from the 12th to the 23rd in section b each defines an angle of 90/12°. Those detectors 122c from the 24th to the 36th in section c each defines an angle of 90/13°. Those detectors 122d from the 37th to the 50th in section d each defines an angle of 90/14° relative to the center C. The distribution of t in this embodiment is shown in FIG. 12. It should be understood that the respective numbers of the detectors in the sections a, b, c and d may be 10, 11, 12 and 13, respectively, which may be disposed with equal spacing. Furthermore, there may be provided 11, 12, 13 and 14 detectors in sections a, b, c and d, respectively, in such way that those 11 detectors in section a may oppose to the 12 detectors in section c, and that the 13 detectors in section b may be arranged to oppose the 14 detectors in section d.

Figure 13:
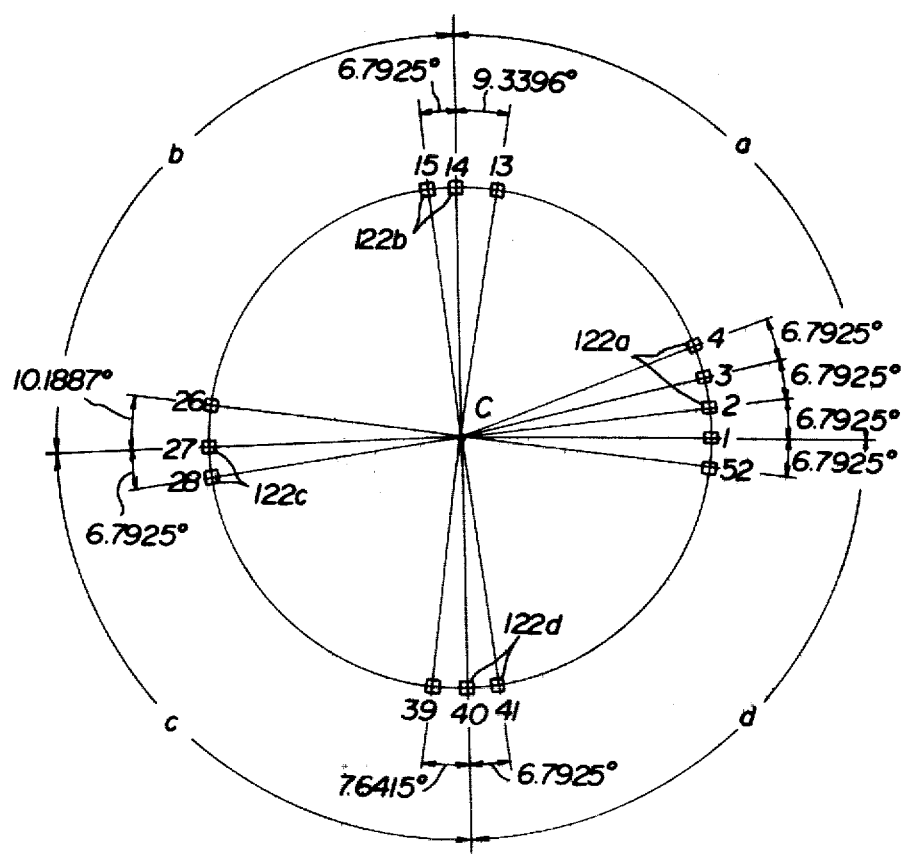
FIG. 13 is an explanatory illustration showing a further detector arrangement.

Alternatively, the gamma ray detectors may be arranged with equal spacing and in equal numbers in each of the four sections, and in such pattern that those neighboring gamma ray detectors located at each boundary between these four sections may be disposed with different spacing, respectively. FIG. 13 shows one such example of arrangement of the gamma ray detectors. There are arranged 13 detectors in each of the 4 sections a, b, c and d. The gamma ray detectors 122a from the first to the 13th in section a are arranged at an angular spacing of 360°÷53=6.7925°. Similarly, the 13th detector in section a and the 14th detector in section b are arranged at an angle of $$6.7925° \left(1 + \frac{6}{16}\right) = 9.3396°.$$

Those detectors 122b from the 14th to the 26th in section b are arranged with an angular spacing of 6.7925°. The 26th detector in section b and the 27th detector in section c are arranged at the angle of $$6.7925° \left(1 + \frac{8}{16}\right) = 10.1887°.$$

Those detectors 122c from the 27th to the 39th in section c are arranged again with the angular spacing of 6.7925°. The 39th detector in section c and the 40th detector in section d are arranged at an angle of $$6.7925° \left(1 + \frac{2}{16}\right) = 7.6415°.$$

Figure 14:
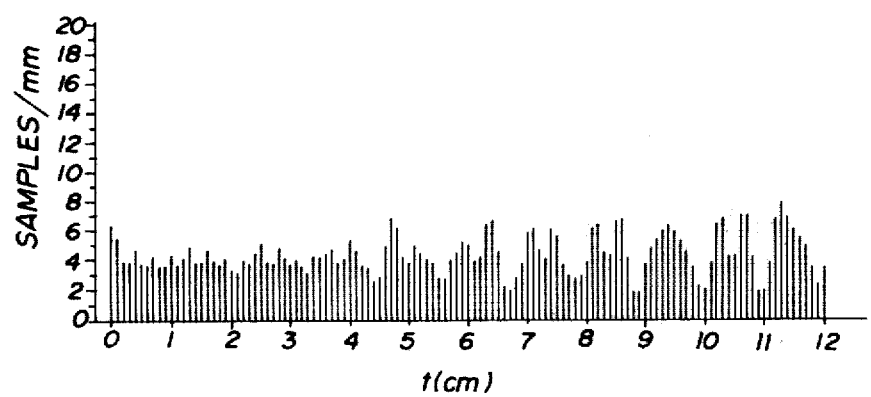
FIG. 14 is an illustration showing the frequency distribution of sampling positions t obtained from the arrangement shown in FIG. 13.

All of the detectors 122d in section d are arranged again with the angular spacing of 6.7925°. It should be understood that the 52nd detector in section d and the first detector in section a are arranged with an angular spacing of 6.7925°. The distribution of t in this embodiment is shown in FIG. 14.

Figure 15:
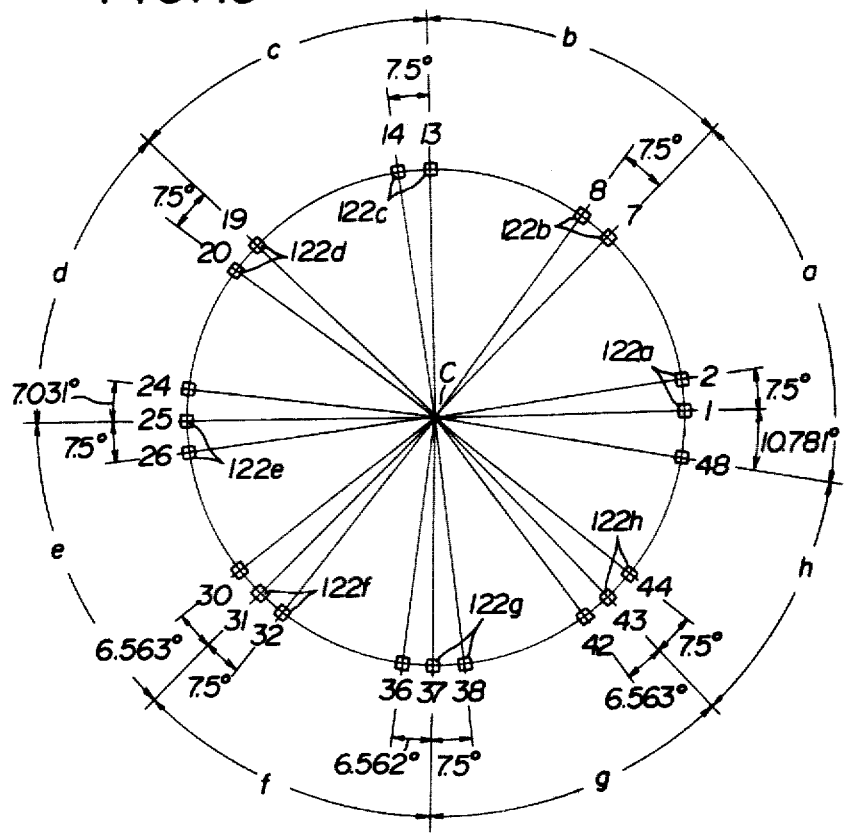
FIG. 15 is an explanatory illustration showing still other detector arrangement.
Figure 16:
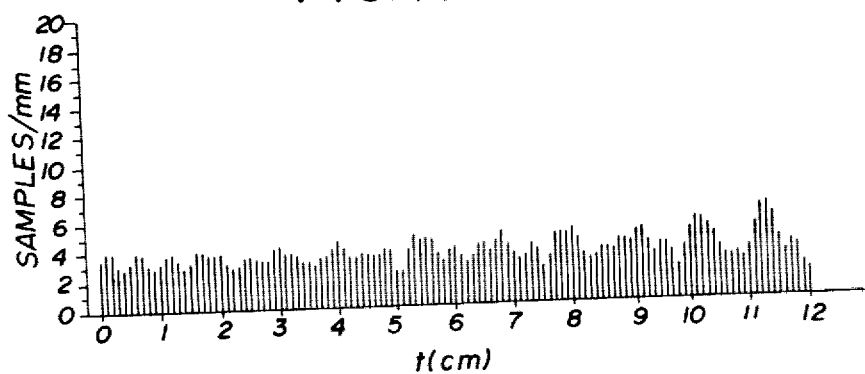
FIG. 16 is an illustration showing the frequency distribution of sampling positions t obtained from the arrangement shown in FIG. 15.

FIG. 15 shows another arrangement of the detectors. In this embodiment, the circular circumference which is co-central with the center C of rotation is divided into 8 sections a, b, c, d, e, f, g and h. In each of these sections, there are provided six (6) gamma ray detectors at angular intervals of 7.5°. Those adjacent detectors between sections a, b, c and d are arranged with an angular spacing of 7.5°, respectively. However, those neighboring detectors located between respective sections d, e, f, g, h and a are arranged with an angular spacing which is not 7.5°, respectively. More particularly, from the first detector in section a to the 24th detector in section d are arranged with angular spacing of 7.5°, respectively. However, the 24th detector in section d and the 25th detector in section e are arranged with an angular spacing of 7.031°. The 30th detector in section e and the 31st detector in section f are arranged with an angular spacing of 6.563°. The 36th detector in section f and the 37th detector in section g are arranged with an angular spacing of 6.562°. The 42nd detector in section g and the 43rd detector in section h are arranged with an angular spacing of 6.563°. And, the 48th detector in section h and the first detector in section a are arranged with an angular spacing of 10.781°. The distribution of t in this embodiment is shown in FIG. 16.

Figure 17:
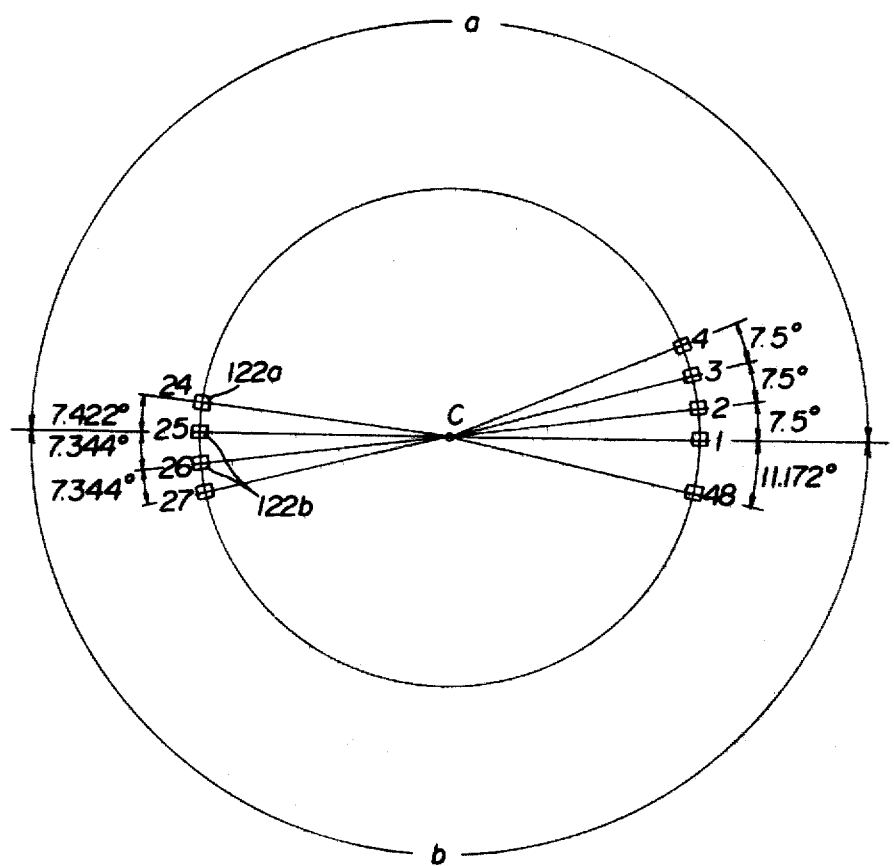
FIG. 17 is an explanatory illustration showing a yet other detector arrangement.
Figure 18:
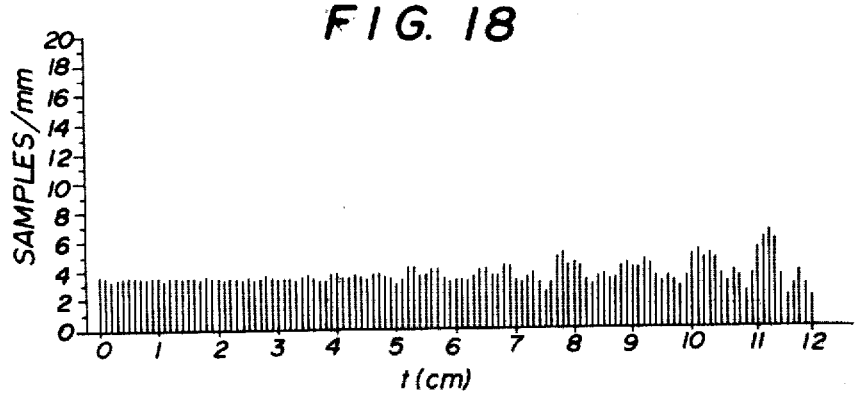
FIG. 18 is an illustration showing the frequency distribution of sampling positions t obtained from the arrangement shown in FIG. 17.

Also, the gamma ray detectors may be arranged so that a same number of them may be provided in each of the two sections on the circular circumference co-central with the center C of rotation, and they may be arranged with equal spacing in each section, but they may be arranged with different spacing between these two sections. FIG. 17 shows such example of arrangement. There are provided 24 detectors in section a, and also there are provided 24 detectors in section b. Those detectors 122a from the first to the 24th in section a are arranged with an angular spacing of 7.5°. The 24th detector in section a and the 25th detector in section b are arranged with an angular spacing of 7.422°. And, those detectors from the 26th and so on are arranged with angular spacing of 7.344°. The 48th detector and the first detector, accordingly, are arranged with an angular spacing of 11.172°. The distribution of t in this embodiment is shown in FIG. 18.

Figure 19:
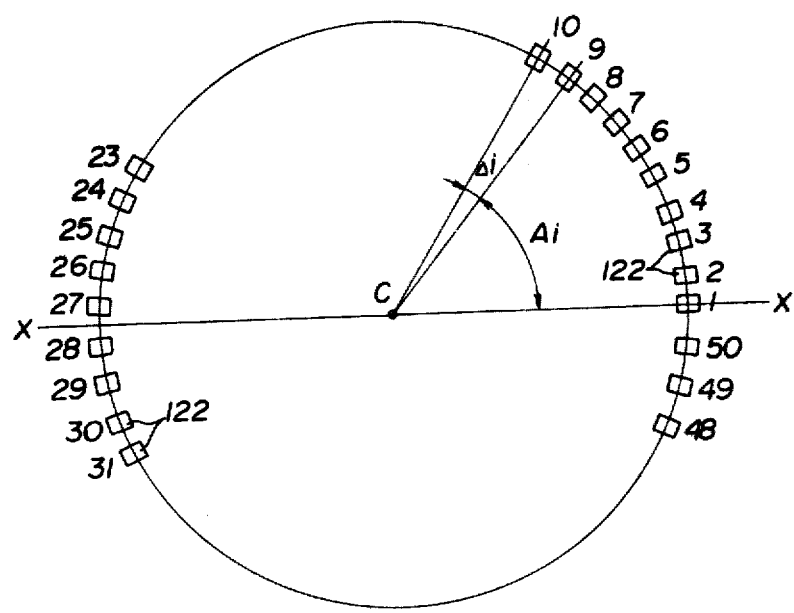
FIG. 19 is an explanatory illustration showing a further detector arrangement.
Figure 20:
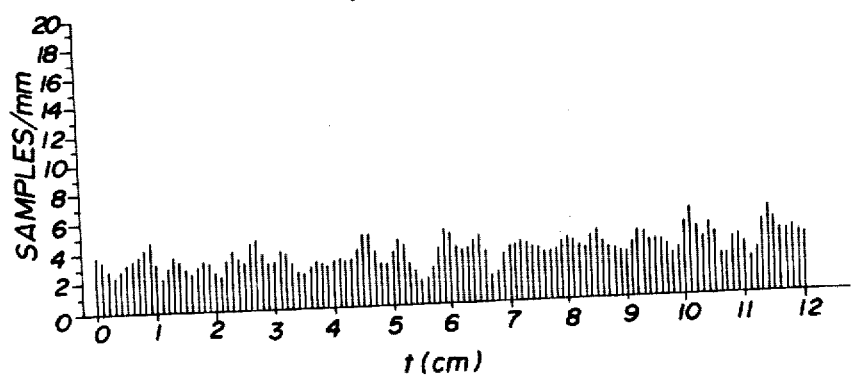
FIG. 20 is an illustration showing the frequency distribution of sampling positions t obtained from the arrangement shown in FIG. 19.

FIG. 19 shows still another arrangement of detectors. This embodiment represents the instance wherein the respective detectors are arranged with different spacing, respectively. The detectors of scintillators are located in a plane intersecting, at right angle, the center C of rotation and are arranged on a circular circumference co-central with the center C. They are arranged in such way that the angle which is defined by a rectilinear line connecting a certain detector and the center C of rotation and by an arbitrary reference rectilinear line XX passing through the center of the circular circumference is $A_i$, and that the angle, i.e. the spacing between detectors, which is defined by a rectilinear line connecting a detector and the center C of rotation and by a rectilinear line connecting the detector which is adjacent to said detector and the center C of rotation is $\Delta_i$. The detector which is located at a position at which the reference rectilinear line XX intersects the circular circumference is assigned the number "1". Those detectors which are located on the circular circumference counter-clockwise therefrom are assigned the numbers 2, 3, 4. Therefore, $A_i$ represents the location of the detector i, and $\Delta_i$ represents the spacing between the detector i and the detector i-1. Fifty (50) detectors are arranged on the circular circumference with the spacings shown in the below-mentioned table and they are adapted to be rotated about the center C. This arrangement of detectors represents one that the spacing $\Delta_i$ along with the location $A_i$ of detectors are varied in regular fashion. The distribution of t in this embodiment is shown in FIG. 20.

TABLE

| No. of detectors | Location of detectors $A_i°$ | Spacing between detectors $\Delta_i°$ | No. of detectors | Location of detectors $A_i°$ | Spacing between detectors $\Delta_i°$ |
|---|---|---|---|---|---|
| 1 | 0.0000 |  | 21 | 134.5539 | 7.0268 |
| 2 | 6.4286 | 6.4286 | 22 | 141.6122 | 7.0583 |
| 3 | 12.8886 | 6.4601 | 23 | 148.7020 | 7.0898 |
| 4 | 19.3802 | 6.4915 | 24 | 155.8233 | 7.1213 |
| 5 | 25.9032 | 6.5230 | 25 | 162.9761 | 7.1528 |
| 6 | 32.4577 | 6.5545 | 26 | 170.1603 | 7.1843 |
| 7 | 39.0437 | 6.5860 | 27 | 177.3761 | 7.2157 |
| 8 | 45.6612 | 6.6175 | 28 | 184.6233 | 7.2472 |
| 9 | 52.3102 | 6.6490 | 29 | 191.9020 | 7.2787 |
| 10 | 58.9907 | 6.6805 | 30 | 199.2122 | 7.3102 |
| 11 | 65.7026 | 6.7120 | 31 | 206.5539 | 7.3417 |
| 12 | 72.4461 | 6.7434 | 32 | 213.9271 | 7.3732 |
| 13 | 79.2210 | 6.7749 | 33 | 221.3318 | 7.4047 |
| 14 | 86.0274 | 6.8064 | 34 | 228.7679 | 7.4362 |
| 15 | 92.8653 | 6.8379 | 35 | 236.2356 | 7.4676 |
| 16 | 99.7347 | 6.8694 | 36 | 243.7347 | 7.4991 |
| 17 | 106.6356 | 6.9009 | 37 | 251.2653 | 7.5306 |
| 18 | 113.5679 | 6.9324 | 38 | 258.8274 | 7.5621 |
| 19 | 120.5318 | 6.9638 | 39 | 266.4210 | 7.5936 |
| 20 | 127.5271 | 6.9953 | 40 | 274.0461 | 7.6251 |
| 41 | 281.7026 | 7.6566 | 46 | 320.4577 | 7.8140 |
| 42 | 289.3907 | 7.6880 | 47 | 328.3032 | 7.8455 |
| 43 | 297.1102 | 7.7195 | 48 | 336.1802 | 7.8770 |
| 44 | 304.8612 | 7.7510 | 49 | 344.0886 | 7.9085 |
| 45 | 312.6437 | 7.7825 | 50 | 352.0286 | 7.9399 |
|  |  |  | 1 | 0.0000 | 7.9714 |

Figure 21:
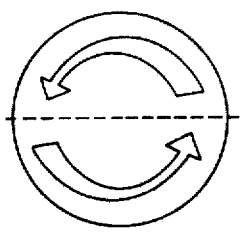
FIG. 21 is an explanatory illustration showing still an other detector arrangement.
Figure 22:
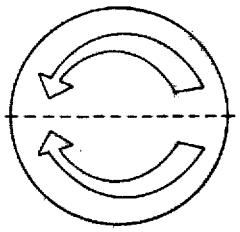
FIG. 22 is an explanatory illustration showing still an other detector arrangement.

FIGS. 21 and 22 show still other arrangements of gamma ray detectors. The detectors are arranged, in each of these embodiments, on an imaginary circular circumference, i.e. circular circumference of slice, co-central with the center C of rotation, and a same number of detectors is provided in each of the two sections obtained by dividing the circular circumference by an imaginary rectilinear line passing through the center of rotation. The detectors in each of the two sections are disposed in such way that their spacing varies regularly as noted in the embodiment of FIG. 19. For example, in FIG. 21, the detectors may be arranged so that the spacing will become progressively wider as they go counter-clockwise in each of these two sections. Alternatively, the spacing arrangement may be symmetrical relative to the imaginary rectilinear line as shown in FIG. 22.

Figure 23:
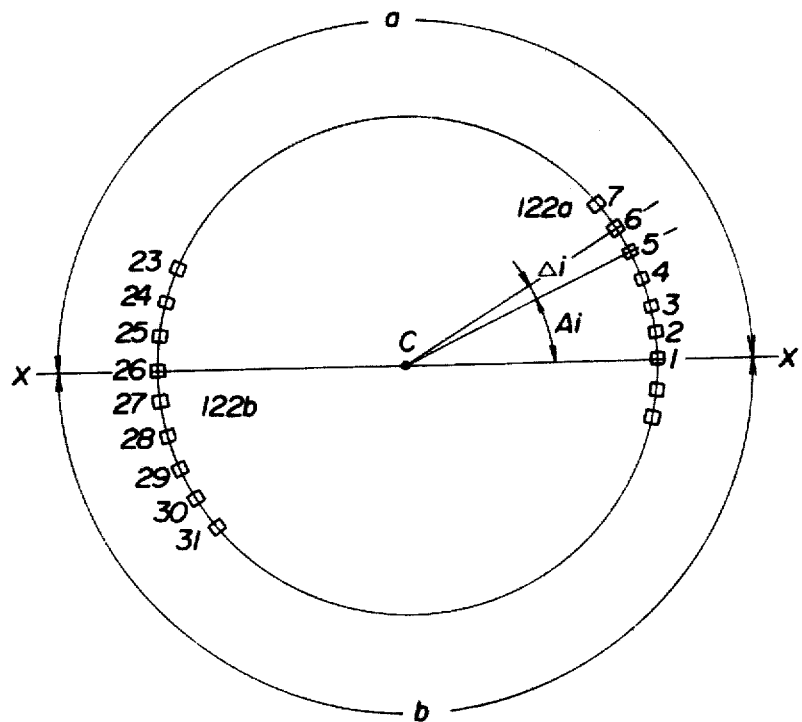
FIG. 23 is an explanatory illustration showing, in further detail, the example of detector arrangement shown in FIG. 22.
Figure 24:
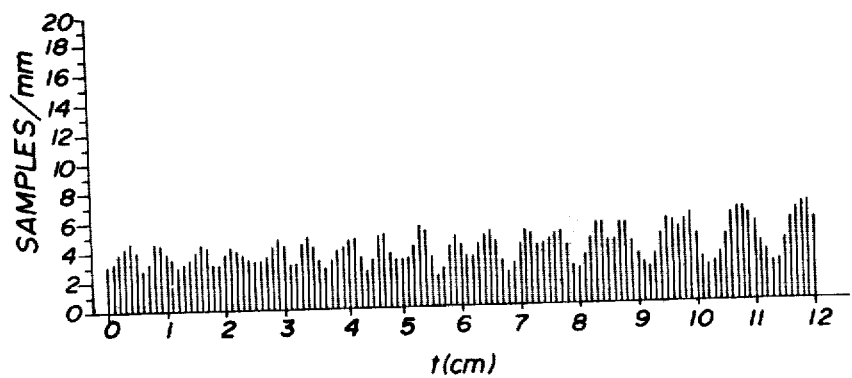
FIG. 24 is an illustration showing the frequency distribution of sampling positions t obtained from the arrangement shown in FIG. 23.

FIG. 23 shows a concrete example of arrangement shown in FIG. 22. As stated above, the detectors are arranged on an imaginary circular circumference co-central with the center C of rotation. There are provided 25 detectors in each of the two sections a and b which are thus divided by an imaginary rectilinear line XX passing through the center of rotation. Those detectors or scintillators 122a which are contained in section a, i.e. those detectors from the first one to the 25th one, and also those detectors 122b of section b, i.e. those detectors from the 26th to the 50th, define such angles, respectively, as those mentioned in the below-given table. The distribution of t in this embodiment is shown in FIG. 24.

TABLE

| No. of detectors | Location of detectors $A_i°$ | Spacing between detectors $\Delta_i°$ | No. of detectors | Location of detectors $A_i°$ | Spacing between detectors $\Delta_i°$ |
|---|---|---|---|---|---|
| 1 | 0.0000 |  | 11 | 67.1786 | 7.0072 |
| 2 | 6.4286 | 6.4286 | 12 | 74.2500 | 7.0714 |
| 3 | 12.9214 | 6.4928 | 13 | 81.3857 | 7.1357 |
| 4 | 19.4786 | 6.5572 | 14 | 88.5857 | 7.2000 |
| 5 | 26.1000 | 6.6214 | 15 | 95.8500 | 7.2643 |
| 6 | 32.7857 | 6.6857 | 16 | 103.1786 | 7.3286 |
| 7 | 39.5357 | 6.7500 | 17 | 110.5714 | 7.3928 |
| 8 | 46.3500 | 6.8143 | 18 | 118.0286 | 7.4572 |
| 9 | 53.2286 | 6.8786 | 19 | 125.5500 | 7.5214 |
| 10 | 60.1714 | 6.9428 | 20 | 133.1357 | 7.5857 |
| 21 | 140.7857 | 7.6500 | 36 | 256.8214 | 7.3928 |
| 22 | 148.5000 | 7.7143 | 37 | 264.1500 | 7.3286 |
| 23 | 156.2786 | 7.7786 | 38 | 271.4143 | 7.2643 |
| 24 | 164.1214 | 7.8428 | 39 | 278.6143 | 7.2000 |
| 25 | 172.0286 | 7.9072 | 40 | 285.7500 | 7.1357 |
| 26 | 180.0000 | 7.9714 | 41 | 292.8214 | 7.0714 |
| 27 | 187.9714 | 7.9714 | 42 | 299.8286 | 7.0072 |
| 28 | 195.8786 | 7.9072 | 43 | 306.7714 | 6.9428 |
| 29 | 203.7214 | 7.8428 | 44 | 313.6500 | 6.8786 |
| 30 | 211.5000 | 7.7786 | 45 | 320.4643 | 6.8143 |
| 31 | 219.2143 | 7.7143 | 46 | 327.2143 | 6.7500 |
| 32 | 226.8643 | 7.6500 | 47 | 333.9000 | 6.6857 |
| 33 | 234.4500 | 7.5857 | 48 | 340.5214 | 6.6214 |
| 34 | 241.9714 | 7.5214 | 49 | 347.0786 | 6.5572 |
| 35 | 249.4286 | 7.4572 | 50 | 353.5714 | 6.4928 |
|  |  |  | 1 | 0.0000 | 6.4286 |

Figure 25:
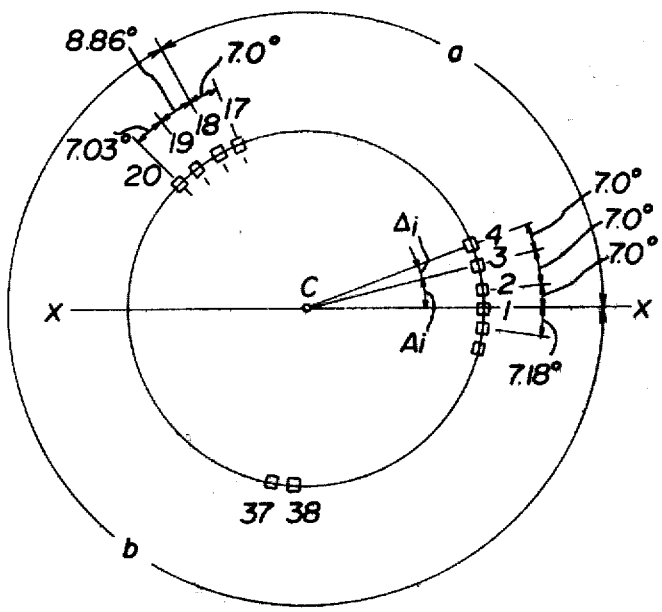
FIG. 25 is an explanatory illustration showing a yet further detector arrangement.
Figure 26:
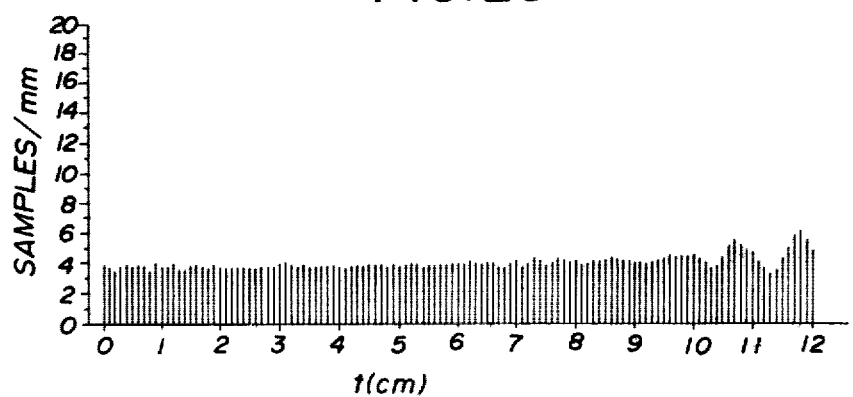
FIG. 26 is a graph showing the frequency distribution of sampling positions obtained from the detector arrangement shown in FIG. 25.

FIG. 25 shows a further embodiment of the position emission computed tomographic apparatus according to the present invention. Under the condition that the sampling density becomes most uniform when the number of detectors provided is 50, that the radius of the ring is 20 cm and that the radius of visual field is 10 cm, the optimum arrangement is sought by the use of a computer, with the result as given in the following table. In this instance, those detectors which are arranged with even spacing are the first to the 18th detectors. The detectors from the 19th to 50th are noted to be arranged with altogether irregular spacing. The sampling density in such arrangement becomes as shown in FIG. 26 by an appropriate smoothing processing, and it will be noted that the density is substantially uniform throughout the entire visual field.

TABLE

| No. of detectors | Location of detectors $A_i°$ | Spacing between detectors $\Delta_i°$ | No. of detectors | Location of detectors $A_i°$ | Spacing between detectors $\Delta_i°$ |
|---|---|---|---|---|---|
| 1 | 359.800 | 7.000 | 11 | 69.800 | 7.000 |
| 2 | 6.800 | 7.000 | 12 | 76.800 | 7.000 |
| 3 | 13.800 | 7.000 | 13 | 83.800 | 7.000 |
| 4 | 20.800 | 7.000 | 14 | 90.800 | 7.000 |
| 5 | 27.800 | 7.000 | 15 | 97.800 | 7.000 |
| 6 | 34.800 | 7.000 | 16 | 104.800 | 7.000 |
| 7 | 41.800 | 7.000 | 17 | 111.800 | 7.000 |
| 8 | 48.800 | 7.000 | 18 | 118.800 | 7.000 |
| 9 | 55.800 | 7.000 | 19 | 127.660 | 8.860 |
| 10 | 62.800 | 7.000 | 20 | 134.690 | 7.030 |
| 21 | 141.700 | 7.010 | 36 | 252.160 | 7.410 |
| 22 | 149.550 | 7.850 | 37 | 259.510 | 7.350 |
| 23 | 157.060 | 7.510 | 38 | 266.610 | 7.100 |
| 24 | 160.840 | 7.780 | 39 | 273.820 | 7.210 |
| 25 | 172.450 | 7.610 | 40 | 280.960 | 7.140 |
| 26 | 179.770 | 7.320 | 41 | 288.330 | 7.370 |
| 27 | 186.770 | 7.000 | 42 | 295.490 | 7.160 |
| 28 | 194.190 | 7.420 | 43 | 302.780 | 7.290 |
| 29 | 201.520 | 7.330 | 44 | 309.790 | 7.010 |
| 30 | 208.750 | 7.230 | 45 | 316.800 | 7.010 |
| 31 | 216.060 | 7310 | 46 | 324.140 | 7.340 |
| 32 | 223.350 | 7.290 | 47 | 331.250 | 7.110 |
| 33 | 230.430 | 7.070 | 48 | 338.400 | 7.150 |
| 34 | 237.540 | 7.120 | 49 | 345.620 | 7.220 |
| 35 | 244.750 | 7.210 | 50 | 352.620 | 7.000 |
|  |  |  | 1 | 359.800 | 7.180 |

The determination of arrangement of detectors by the use of an electronic computer is as follows. Firstly, a certain arrangement is given, and the distribution of its sampling density is obtained. Then, appropriate indices showing the fineness of its distribution and showing the uniformity are defined. The locations of the respective detectors are adjusted one after another so that starting from an arbitrary arrangement such as arrangement with equal spacing, and finally reaching the level that said indices become maximum, and thus the locations of all the detectors are corrected, and furthermore such process is repeated again and again, and this is called "sequential search method". These indices are, for example, FOM which is obtained from the following formula:

$$FOM = 1 / \sqrt{ \sum_k \left( \frac{1}{s(t_k)} \right) \sum_k s(t_k) } \quad (3)$$

wherein $t_k$ represents a digitalized value of t obtained by separating the value of t at a certain interval, $s(t_k)$ represents a sampling density distribution which is expressed as a function of $t_k$, and the symbol $\Sigma$ means an addition to be made with respect to the extent of $t_k$ which, in turn, is determined by a necessary field of view of measurement.

Figure 27:
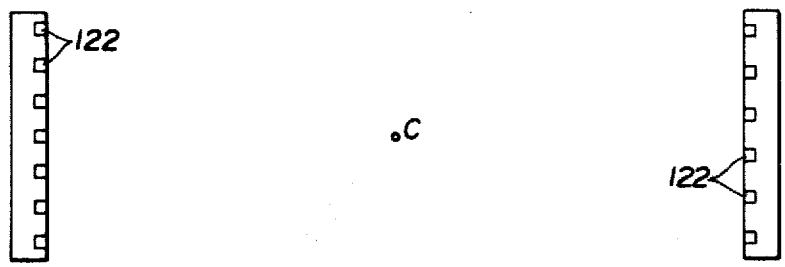
FIG. 27 is an explanatory illustration showing a still other detector arrangment.
Figure 28:
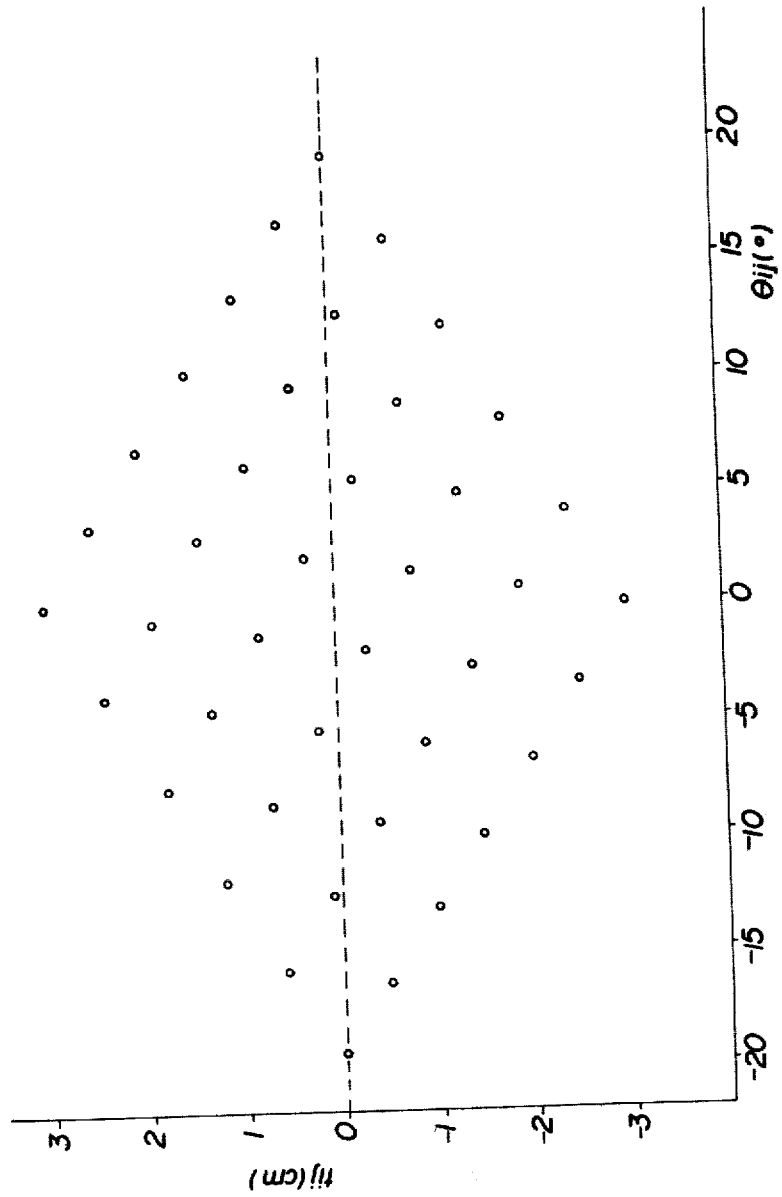
FIG. 28 is a graph showing the distribution of sampling positions obtained from the detector arrangement shown in FIG. 27.

The arrangement of detectors may be such as is comprised of at least one pair of arrays of detectors which are disposed to oppose each other about the center of rotation and in such way that the spacing between the detectors in one of the arrays are different from the spacing of the detectors in the other one of the arrays. FIG. 27 shows an example of such arrangement. In this embodiment, the detectors are comprised of two arrays of detectors which are disposed to oppose each other on an imaginary plane passing, at right angle, the center axis C of rotation. One of the detector arrays is comprised of 6 detectors which are arranged with equal spacing, and the other detector array is comprised of 7 detectors, in this Figure. It will be appropriate to employ a greater number of detectors than those mentioned above, in order to be practical. Here, however, a number which is of the order sufficient for the explanation of the aimed advantage is selected. These two detector arrays are constructed so as to rotate with respect to the center C without changing their relative positions. The respective detectors belonging to one of the two arrays are coupled by coincidence circuits to all of the detectors belonging to the other one of the arrays. The distribution of the sampling positions obtained from such arrangement of detectors is shown in FIG. 28. The rotation of these detector arrays correspond to parallel translation or movement, along the horizontal axis, of a group of small round marks which indicate sampling positions in FIG. 28. In such detector arrangement as mentioned in FIG. 28, it should be understood that, by rotating the detectors about the center C, it is apparent that hardly any sampling positions become superposed and the frequency of occurrence of distance t is reduced to one severalth as compared with the conventional technique using same number of detectors in both of the arrays.

Figure 1:
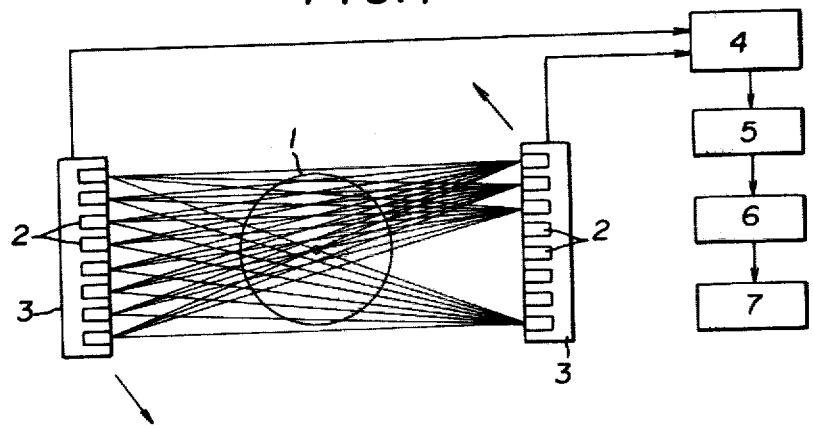
FIG. 1 is an explanatory illustration showing a general structure of a positron emission computed tomographic apparatus.
Figure 2:
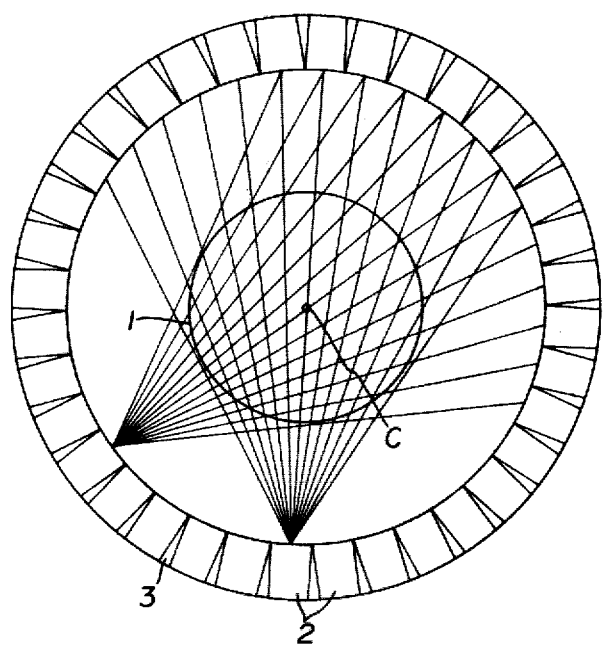
FIG. 2 is an explanatory illustration showing the arrangement of gamma ray detectors in a known scanner for positron emission computed tomography.
Figure 29:
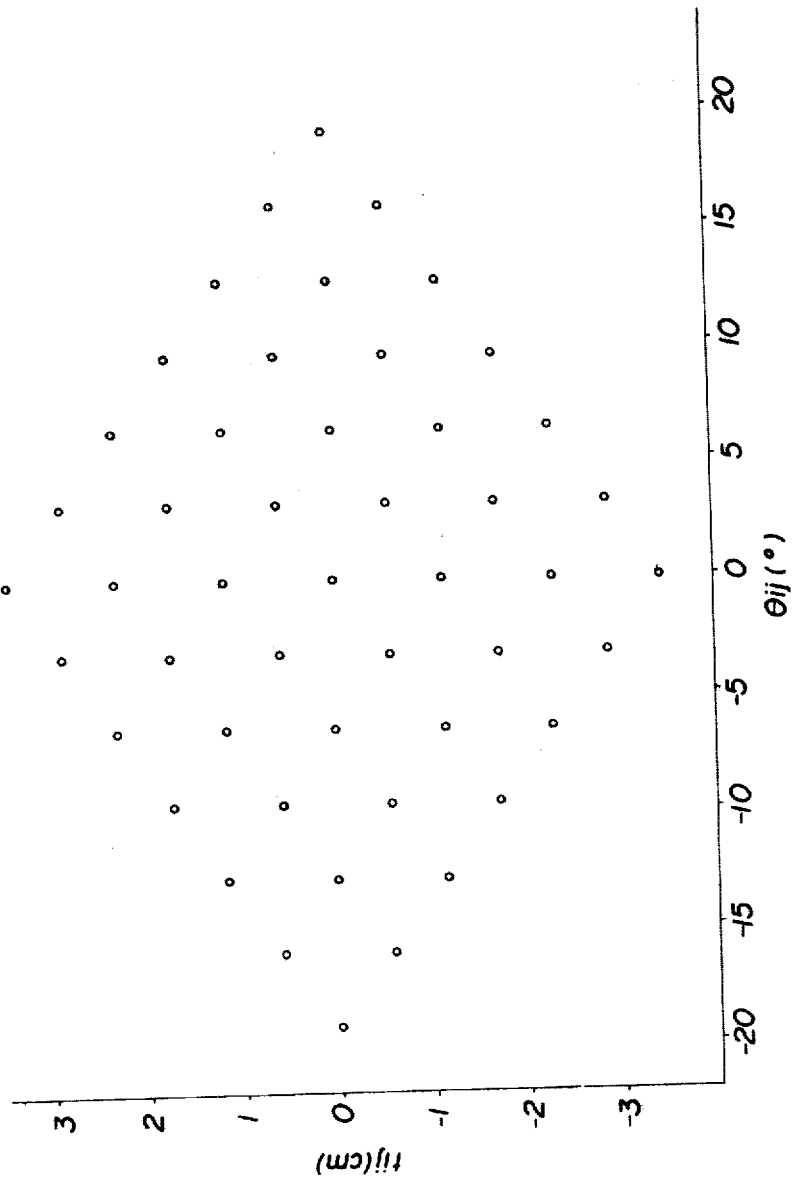
FIG. 29 is a graph showing the distribution of the sampling positions obtained from a known arrangement wherein the arrays of detectors are comprised of detectors which are disposed at equal spacing.

Just for the purpose of reference, the distribution of sampling positions in an arrangement wherein the detectors contained in each of the arrays are distributed with equal spacing and in a same number, such as in the case of the arrangement shown in FIG. 1, is shown in FIG. 29.

The detectors may be arranged in such way that at least one pair of detector arrays which are disposed to oppose each other are arranged at different distances from the center of rotation, respectively. In such an instance, the number and the spacing of the detectors in each detector array may be the same or different. Also the respective detector arrays may be provided in parallel or non-parallel.

Figure 30:
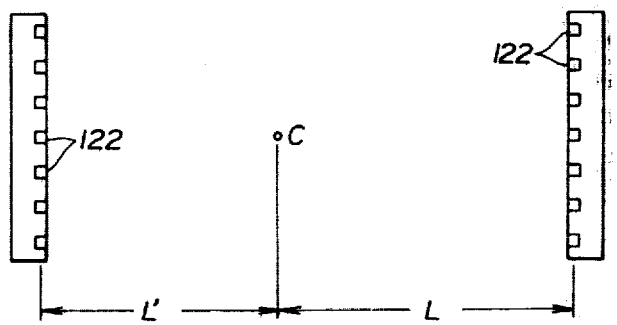
FIG. 30 is an explanatory illustration showing a further arrangement of detectors.

Fig. 30 shows an example of such arrangement. The detectors are comprised of two detector arrays which are provided to oppose each other and in parallel relative to the center C of rotation. Each of these detector arrays is comprised of 7 detectors which are arranged with equal spacing. However, from the viewpoint of practical use, each array is comprised of a greater number of detectors. These two detector arrays are arranged so that the ratio of their distances from the center C of rotation, i.e. the ratio of the distances L and L' in FIG. 30, is selected to be 5:4. It is needless to say that the respective arrays of detectors are rotated with respect to the center C without changing their relative positions. Also, each of the detectors belonging to one of the detector arrays is coupled by coincidence counting circuit to all of the detectors belonging to the other detector array. The distribution of sampling positions which is obtained from such arrangement is shown in FIG. 31. The rotation of these arrays of detectors correspond to a parallel translation or movement, along the horizontal axis, of a group of small circular marks indicating the sampling positions in the drawing.

In the arrangement as shown in which the distances from the center of rotation to the two detector arrays are different from each other, it should be noted that, by rotating the detectors about the center C, almost no sampling positions will become superposed. The frequency of occurrence of distance t may be reduced to one severalth as compared with the arrangement wherein the respective detector groups are comprised of detectors arranged with equal spacing and in the same number and arranged at the same distance from the center of rotation.

In the above-described embodiments, data are collected by rotating the gamma ray detectors through 360°. Such pattern of operation may be modified and there may be made a measurement by bringing the detectors to a halt for each appropriate angle, and thereafter this measurement may be repeated by further rotation.

Furthermore, such rotation is not limited to a single revolution. During the process of measurement, the rotation may be made either in a single direction or in alternate directions, i.e. in reversed directions, through 360°, in repeated fashion. Even in case the range of angle of rotation is less than 360°, there can be obtained much better sampling characteristic as compared with known apparatuses. Therefore, there may be performed reciprocating rotation scanning through an angle less than 360°.

What is claimed is:

1. A scanner for positron emission computed tomography, comprising:
   a rotary member rotatable within a plane of a slice about an axis perpendicular to this slice plane and having means to accommodate a subject for examination;
   a drive means for rotating said rotary member in said slice plane; and
   radiation detectors provided on said rotary member with the intervention by the center of rotation of the rotary member in between these detectors, said radiation detectors being arranged so that the spacing of at least a part of these detectors is irregular than the spacing of the rest of the detectors.

2. A scanner according to claim 1, wherein:
   said detectors are arranged on a circular circumference co-central with the center of rotation of the rotary member at an equal distance therefrom, and wherein:
   these detectors are arranged so that at the end of one whole revolution through 360° of the rotary member, these detectors are brought into positions in agreement with their positions before such rotation.

3. A scanner according to claim 2, in which:
   the detectors are arranged with equal spacing in each of sections obtained by dividing said circular circumference on said plane by at least one rectilinear line passing through said center of rotation and located in said plane, and in which:
   the spacing between the detectors in one of these sections is different from the spacing in the other of the sections.

4. A scanner according to claim 3, in which:
   said sections are comprised of two sections divided by a single rectilinear line.

5. A scanner according to claim 3, in which:
   the sections are comprised of four sections divided by two rectilinear lines.

6. A scanner according to claim 2, in which:
   a same number of detectors is arranged with equal spacing in each of sections separated by a plurality of rectilinear lines passing through the center of rotation and located in said plane, and in which:
   the detectors are arranged at equal spacing excepting those located at a boundary region between respective neighboring sections, and wherein:
   the spacing between the detectors located at the boundary region between respective neighboring sections are different from each other.

7. A scanner according to claim 6, in which:
   the sections are comprised of four sections divided by two rectilinear lines.

8. A scanner according to claim 2, in which:
   a plurality of detectors are arranged in each of sections divided by a plurality of rectilinear lines passing through the center of rotation of the rotary member and located in said plane, and in which:
   the spacing between the detectors is identical in some successively neighboring sections, and those detectors in the remaining successively neighboring sections are arranged with the same spacing as that for said some sections excluding the spacing between neighboring detectors located at the boundary region between these remaining respective sections, and in which:
   the spacing between the adjacent detectors located at the boundary region between these remaining respective sections is different from that in said some sections.

9. A scanner according to claim 8, in which:
   the sections are comprised of eight sections divided by four rectilinear lines, and in which:
   said neighboring some sections are each provided with four sections.

10. A scanner according to caim 2, in which:
    the detectors are arranged in a plural number in each of sections divided by at least one rectilinear line passing through the center of rotation of the rotary member and located in said plane, and in which:
    the spacing between the detectors is different between each of these sections.

11. A scanner according to claim 10, in which:
    the sections are comprised of two sections divided by a single rectilinear line.

12. A scanner according to claim 2, in which:
    the detectors are arranged so that the angles defined by adjacent detectors are different from each other relative to the center of rotation.

13. A scanner according to claim 12, in which:
    the detectors are arranged so that said angles vary regularly.

14. A scanner according to claim 13, in which:
    the detectors are arranged so that said angles increase progressively.

15. A scanner according to claim 2, in which:
    the detectors are arranged so that a plural number of them is included in each of sections divided by at least one rectilinear line passing through the center of rotation and located in said plane, and in which:
    these detectors have progressively varying spacings.

16. A scanner according to claim 15, in which:
    the sections are comprised of two sections divided by a single rectilinear line, and in which:
    the spacing between the detectors in one of these two sections becomes progressively narrower, whereas in the other of the sections the spacing between the detectors becomes progressively narrower.

17. A scanner according to claim 15, in which:

the sections are comprised of two sections divided by a single rectilinear line, and in which:

the spacing between the detectors in one of these two sections becomes progressively narrower, whereas in the other one of the sections the spacing between the detectors becomes progressively wider.

18. A scanner according to claim 2, in which:

at least a part of neighboring detectors are arranged with irregular spacing.

19. A scanner for positron emission computed tomography comprising: a rotary member rotatable in a slice plane about a center axis perpendicular to this slice plane and having means for accomodating a subject for examination, a drive means for rotating this rotary member in said slice plane, and at least a pair of detector arrays provided on the rotary member to oppose each other with the center of rotation of this rotary member lying inbetween, those detectors in one of said detector arrays being arranged with spacing different from the spacing between the detectors in the other one of the detector arrays.

20. A scanner according to claim 19, in which:

said pair of detector arrays are arranged in parallel with each other.

21. A scanner according to claim 20, in which:

said arrays of detectors are provided as a pair.

22. A scanner for positron emission computed tomography, comprising:

a rotary member rotatable in a slice plane about a center axis perpendicular to this slice plane and having means for accomodating a subject for examination, a drive means for rotating said rotary member in said slice plane, and at least a pair of detector arrays which are arranged to oppose each other at different distances from the center of rotation of the rotary member.

23. A scanner according to claim 22, in which:

said pair of detector arrays are arranged in parallel with each other.

24. A scanner according to claim 23, in which:

said detectors are provided as a pair.

* * * * *